United States Patent [19]

Hanna

[11] Patent Number: 5,441,511
[45] Date of Patent: Aug. 15, 1995

[54] KERATOTOME FOR PERFORMING ARCUATE INCISIONS

[76] Inventor: Khalil Hanna, 19, rue las Cazes, 75007 Paris, France

[21] Appl. No.: 934,740
[22] PCT Filed: Apr. 11, 1991
[86] PCT No.: PCT/FR91/00300
   § 371 Date: Aug. 30, 1993
   § 102(e) Date: Aug. 30, 1993
[87] PCT Pub. No.: WO91/16023
   PCT Pub. Date: Oct. 31, 1991

[30] Foreign Application Priority Data

Apr. 12, 1990 [FR] France .................. 90 04722

[51] Int. Cl.$^6$ ............................. A61B 17/32
[52] U.S. Cl. ................................. 606/166
[58] Field of Search .......... 606/166, 161, 180

[56] References Cited

U.S. PATENT DOCUMENTS

| | | | |
|---|---|---|---|
| 4,205,682 | 6/1980 | Crock et al. | 606/166 |
| 4,423,728 | 3/1984 | Lieberman . | |
| 4,608,977 | 2/1986 | Brown . | |
| 4,648,400 | 10/1987 | Schneider . | |

FOREIGN PATENT DOCUMENTS 0047190 10/1982 European Pat. Off. .

OTHER PUBLICATIONS

Arch Ophtalm. vol. 106, Aot 1988, U.S. pp. 1130–1135 Duffey et al.: 'paired arcuate keratotomy' voir p. 1134 colonne 2, ligne 46–collone 3, ligne 2.

*Primary Examiner*—Michael H. Thaler
*Attorney, Agent, or Firm*—Griffin, Butler, Whisenhunt & Kurtossy

[57] ABSTRACT

The present invention relates to a keratotome for forming arcuate incisions in a cornea for the purpose of correcting astigmatism. To this end, the keratotome (3) comprises a tubular outer support (4) containing a tubular inner body (6) that is capable of rotating relative thereto and that in turn contains at least one blade (82) capable of projecting by a predetermined amount relative to a reference surface (13) whereby the tubular outer support (4) bears against the cornea (2). In order to make arcuate incisions of determined angular position and of determined angular length, the support (4) and the body (6) have means (108) for determining their relative angular position.

9 Claims, 5 Drawing Sheets

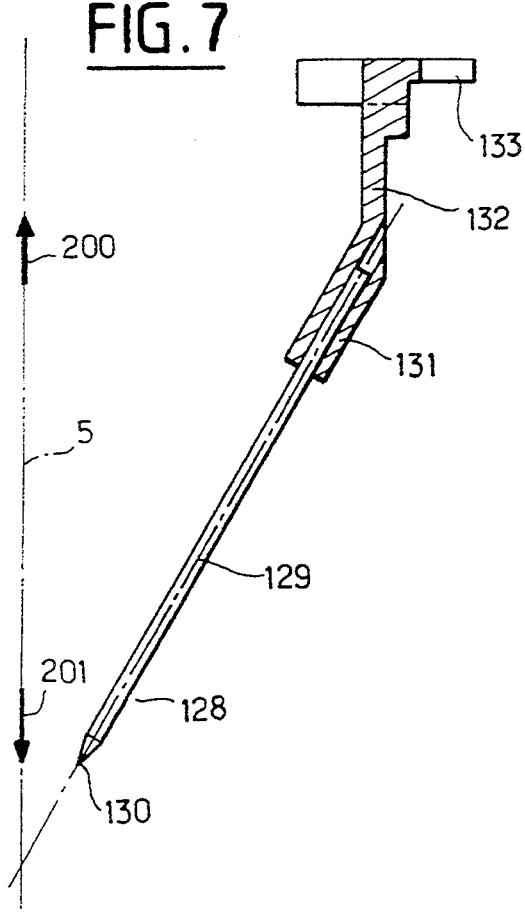
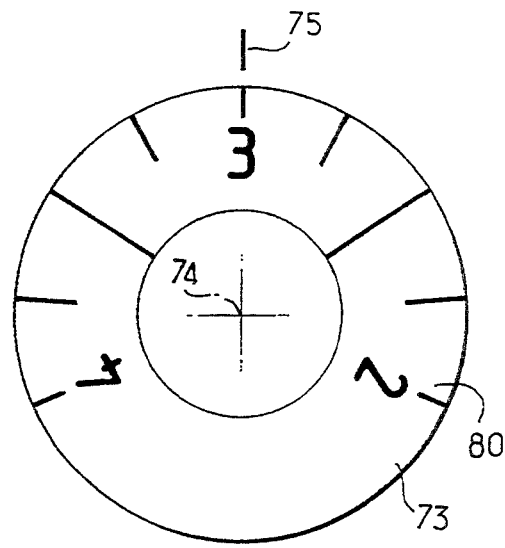
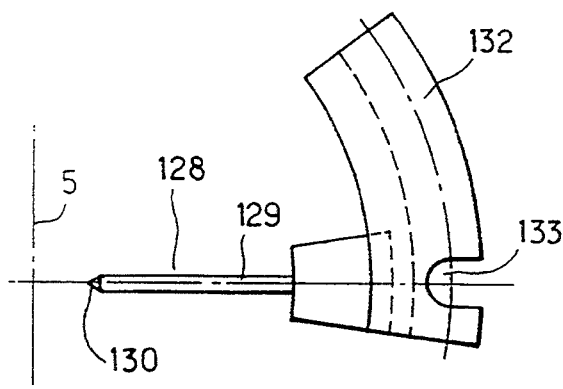
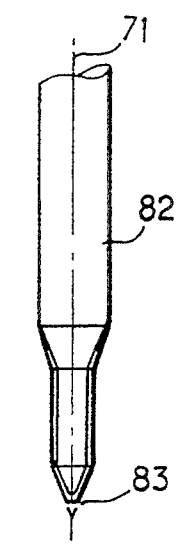
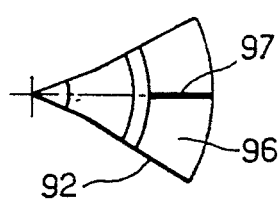

KERATOTOME FOR PERFORMING ARCUATE INCISIONS

The present invention relates to a keratotome for performing arcuate incisions in a cornea in order to correct astigmatism.

BACKGROUND OF THE INVENTION

Astigmatism in an eye is the result of two mutually perpendicular meridians of the anterior face of the cornea not having the same curvature, and a known method of correcting astigmatism consists in forming two incisions in the cornea perpendicularly to the most highly curved meridian, i.e. to the meridian with the shorter radius of curvature, said two incisions being disposed respectively on opposite sides of the optical zone.

Merlin ("Curved keratotomy procedure for congenital astigmatism"; Journal of Refractive Surgery, 1987; 3:92–97) has made arcuate incisions for the purpose of correcting astigmatism, by using a micrometer blade held manually while using visual guidance based on a mark previously made by means of a circular marker.

Nevertheless, it is difficult to make incisions of uniform depth by means of a blade that is merely held in the hand, and this is particularly true when said incisions are situated on a diameter that is small.

As a result, such arcuate incisions are little used.

An object of the present invention is to make it possible to form arcuate incisions that are sufficiently accurate to achieve results regardless of the dexterity of the surgeon.

SUMMARY OF THE INVENTION

The present invention seeks to solve the stated object by mechanical means and, to this end, it provides a keratotome for making an incision in a cornea and comprising, for this purpose, in conventional manner for keratoplasty trephines:

- an envelope-forming tubular outer support having a determined axis and including, for application against a cornea, an annular base portion that is circularly symmetrical about the axis of the support and that defines a reference geometrical surface determined by the shape presented by the cornea when the support has its base portion pressed thereagainst;
- a tubular inner body disposed coaxially inside the support and set back towards the inside of the support relative to the reference surface;
- guide means for guiding the body in rotation about the axis relative to the support;
- drive means for driving the body in rotation about the axis relative to the support;
- a blade disposed inside the body and extending along a longitudinal direction, the blade having a sharp tip in a determined direction relative to its longitudinal direction; and
- means for providing a connection between the blade and the body, said means including means for displacing the blade in controlled manner in translation along its longitudinal axis relative to the body between a rest position, in which it is set back towards the inside of the support relative to the reference surface, and in which the tip is directed towards said reference surface, and in a cutting position where the tip projects outside from the support relative to the reference surface, in a manner that is offset relative to the axis of the support; characterized in that in order to perform arcuate incisions of determined angular position and of determined angular length, the support and the body have determining means for determining their relative angular position.

It will readily be understood that such a keratotome makes it possible to make incisions that are exactly in the form of a circular arc, and as a result that relate to a zone in which the cornea is of substantially constant thickness, and also makes it possible, without difficulty, to control two important parameters, namely the angular length of the incision, and the depth of the incision which is adjusted by adjusting the extent to which the tip of the blade projects out from the body, when in the cutting position.

Other characteristics and advantages of a keratotome of the invention appear from the following description of a non-limiting embodiment described with reference to the accompanying drawings which form an integral part of the present description.

BRIEF DESCRIPTION OF THE DRAWINGS

FIGS. 6 and 7 are respectively a plan view as seen in the direction marked by arrow II in FIG. 1 and a section view on the plane marked IX—IX in FIG. 2 and including the axis of rotation of the body, showing the means for marking the astigmatism axis.

FIG. 8 is a view as seen in the direction of arrow X in FIG. 1, showing a detail of the micrometer means for separating respective zones of the blade carrier and of the body, thereby enabling the extent to which the tip of a blade is offset relative to the axis of relative rotation between the body and the support.

FIG. 9 shows a detail view of a blade as seen in the direction marked by arrow XI in FIG. 1.

FIG. 10 is a view in the direction marked by arrow XII in FIG. 1 showing a detail of the means for displacing the blade adjustably in translation along its own direction, i.e. for adjusting the extent to which the tip of the blade projects out from the support relative to the reference surface when the blade is in its cutting position.

DESCRIPTION OF PREFERRED EMBODIMENTS

Figure 1:
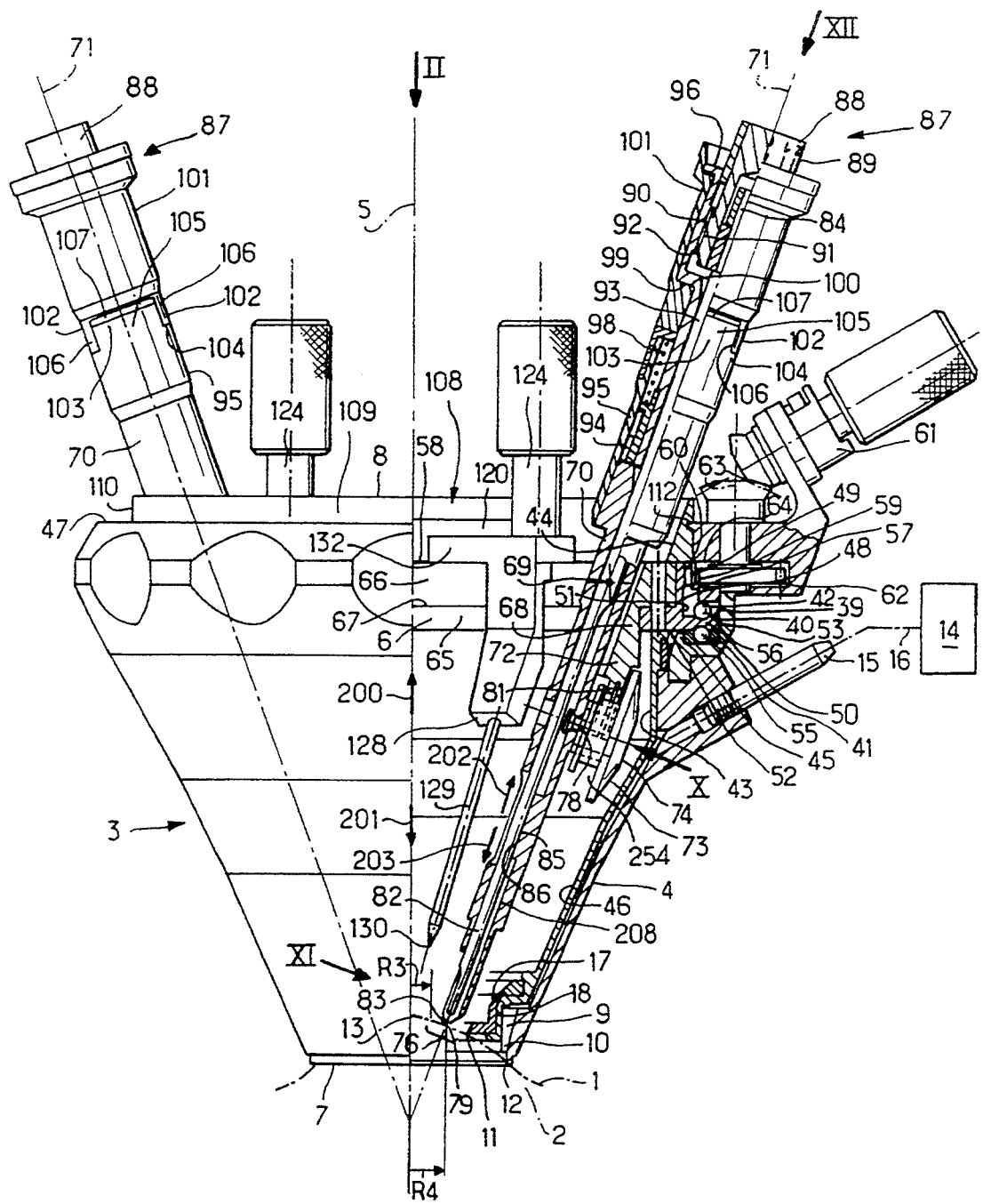
FIG. 1 shows a keratotome of the invention, half in side elevation and half in section on a plane marked I—I in FIG. 2, and including the relative axis of rotation between the inner body and the outer support, which axis coincides with the visual axis while the keratotome is in use.

The keratotome shown is of a type comprising two blades, but it will naturally be understood that providing a keratotome having only one blade or possibly have more than two blades would not go beyond the ambit of the present invention.

For the purpose of being grasped in the hand of the surgeon and for enabling it to be positioned on the anterior face 1 of the cornea 2 to be incised, the keratotome shown 3 includes an outer support 4 which is generally in the form of a tubular frustoconical wall that is symmetrical about an axis 5 and that surrounds an inner body or carriage 6 which is also in the form of a tubular wall that is symmetrical about the axis 5 and that is rotatably mounted inside the support about said axis 5, with any other type of relative displacement therebetween being prevented.

The outer support 4 flares from a base portion 7 that is intended to be pressed against the anterior face 1 of the cornea 2 to be incised, around the location of the incisions to be made, and it extends to a head portion 8 that is intended to be held by the non-dominant hand of the surgeon.

The wall constituting the base portion 7 of the outer support 4 includes an annular cavity 9 that is circularly symmetrical about the axis 5 and that opens out into the base portion 7 via an annular slot 10 which is defined between two annular bearing surfaces 11 and 12 that are circularly symmetrical about the axis 5 and that lie on the same reference surface 13. The reference surface 13 is chosen to correspond with the anterior face 1 of most corneas 2. A suction effect towards the inside of the cavity 9 is provided through the slot 10 by connecting said cavity 9 to means 14 suitable for establishing a reduced pressure therein, said means being connected to the cavity 9 by a coupling 15 therefor on the outside of the support 4, and by a flexible hose 16.

The bearing surface 11 closer to the axis 5 is preferably constituted by an annular part 17 rotatably mounted on the support 4 in an annular groove 18 thereof facing the axis 5. This groove is delimited by two dismountable parts so as to enable the part 17 shown in FIGS. 1, 4, and 5 to be changed.

The part 17, or any other part that may be substituted therefor, comprises a peripheral skirt 20, 21 that constitutes a circularly symmetrical annulus about the axis 5 that is closely complementary in shape to the shape of the groove 18. Inside the skirt 20 or 21, the part 17 has a wall delimited by a plane top face 22, 23 perpendicular to the axis 5, and having determined shapes on its other face lying flush with the reference surface 13.

Figure 5:
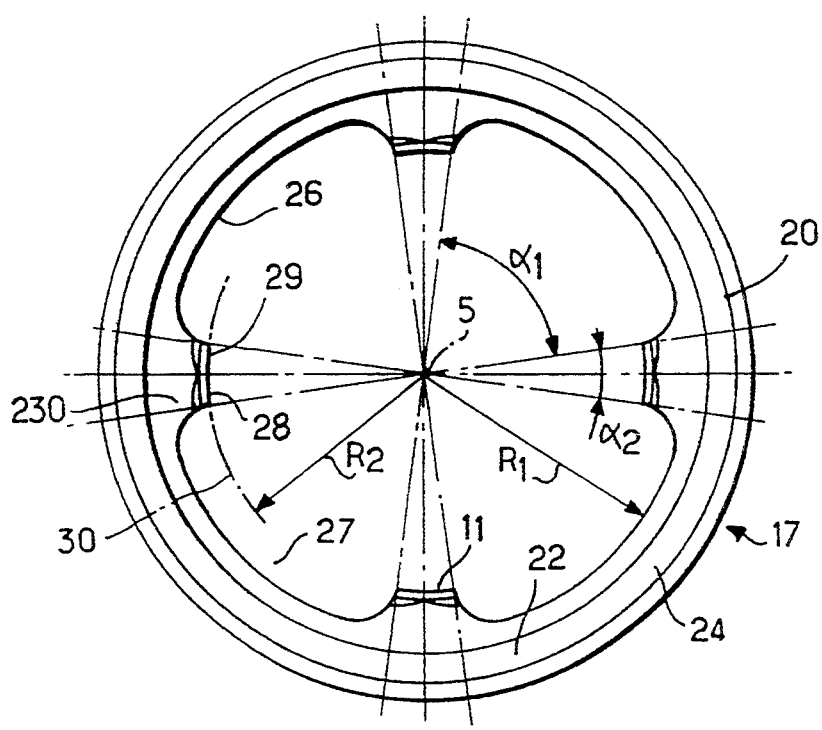
FIG. 5 shows the same means in plan view, e.g. as seen in the direction marked by arrow II in FIG. 1.
Figure 4:
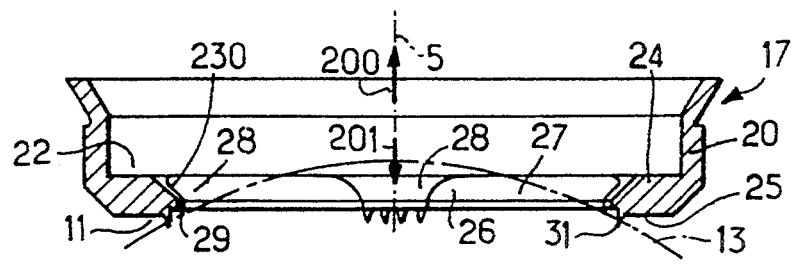
FIG. 4 is a section on a plane including the axis of rotation between the body and the supports, such as the plane I—I of FIG. 2, and shows a first embodiment of means for marking the position of the keratotome relative to the cornea.

Thus, as shown more particularly in FIGS. 4 and 5, the part 17 has a transverse wall in the form of a ring 24 delimited by two plane faces 22 and 25, and by an annular edge 26. Four zones 27 disposed on the same geometrical cylindrical (not referenced) of radius $R_1$, and of angular extent $\alpha_1$ close to 90°, alternate with four zones 28 of angular extent $\alpha_2$ of the order of a few degrees. Each of these zones 28 carries an edge 29 on its face 25, said edge being an arc of a circle 30 of radius $R_2$ smaller than $R_1$ and, in practice, greater than the radius of the transparent zone of the cornea.

The four edges 29 enable the keratotome 3 to be accurately placed on the cornea 2 after the cornea has previously been marked with circles centered on the visual axis. The four edges 29 lie flush with the reference surface 13 and together they constitute the bearing surface 11 that comes into contact with the anterior face 1 of the cornea 2 on the circular markings having the same radius as the circle 30.

The part 17 may also include, projecting from its face 25 in the immediate proximity of each edge, a group of teeth 31 that prevent the keratotome from sliding over the anterior face 1 of the cornea. The part 17 is also completely situated in a position that is set back relative to the reference surface 13.

The outer support 4 includes another internal annular groove 39 in its head zone 8, having a bottom 40 of diameter that is as large as possible given the dimensions of the head portion 8. The groove 39 includes two plane flanks 41 and 42 perpendicular to the axis 5. The flanks 41 and 42 open out onto respective faces 43 and 44 of the outer support 4, which faces are circularly symmetrical cylinders about the axis 5 which they face, directly in the case of the flank 42 and via a rim 45 in the case of the flank 41. Beneath the face 43, the support 4 includes a tapering face 46 that converges towards its base portion 7. The outer support 4 is delimited at its top by a plane face 47.

The above-described support 4 is advantageously made up of a plurality of parts that are assembled together by means enabling them to be taken apart at will, thereby enabling the support to be cleaned easily. In particular, the head portion 8 and the base portion 7, although they are secured to each other, can be taken apart at will at the shoulder 45 so as to give access to the adjustment means that are described below.

The outer support 4 co-operates with the groove 39 and the face 44 co-operates with the inner body 6 to guide the inner body in rotation about the axis 5 without any possibility of relative translation.

To this end, the body 46 carries a cylindrical face 48 of diameter slightly less than that of the face 44, which faces are disposed to face each other without mutual contact. The face 48 carries two shoulders 49 and 50 which project radially and which are placed respectively facing the face 44 and facing the groove 39 in which the shoulder 50 is engaged. The shoulder 50 is defined by plane annular faces 51 and 52 and by a cylindrical outer peripheral face 53 sliding over the bottom 40 of the groove 39.

The faces 52 and 51 of the shoulder 50 bear respectively against the flanks 41 and 42 via a ball bearing 55, 56. The shoulder 49 is delimited by plane annular faces 57 and 58 and by a face 59 that is generally in the form of a circularly symmetrical cylinder about the axis 5, having a diameter substantially equal to that of the face 44 so as to establish further guidance of the body 6 and of the support 4 in mutual rotation about the axis 5 by means of a sliding contact. The face 59 is indented with meshing teeth 60 that are regularly spaced apart angularly about the axis 5 for co-operating with manual drive means 61 of conventional design, e.g. as described in Document EP 0 047 190, to co-operate with the meshing teeth 60 of the body 6 via a gear wheel 62 rotatably mounted on the support 4 about an axis 63 parallel to the axis 5, which gear wheel 62 passes locally through the face 44 of the support 4 towards the axis 5 via an opening 64 in said face 44.

It may be observed that because of the above-described disposition and when the base portion 7 is separated from the head portion 8 at the shoulder 45, the body 6 of the keratotome 3 remains assembled to the head portion 8 which also carries the manual drive means 61.

Via faces 65, 66, and 67 defining an internal shoulder, the body 6 bears securely against two identical and diametrically opposite yokes 68, preferably in a configuration that can be disassembled for maintenance purposes. Each of the yokes 68 allows a corresponding blade carrier 70 to be rotatably mounted about a hinge axis 69 relative to the body 6. The two axes 69 are situated perpendicularly to a common plane 205 including the axis 5 and coinciding with the plane marked I—I in FIG. 2, the two axes 69 being symmetrically disposed about a plane 204 that also includes the axis 5 but that is perpendicular to the plane 205, and they are situated both as far away as possible from the axis 5 and as close as possible to the face 58 of the shoulder 49 of the body 6, i.e. from the face 47 of the head portion 48 of the support 4, so as to enable them to be as far away as possible from the base portion 7 thereof.

In the plane 205 including the axis 5 and perpendicular to the axes 69, the blade carrier 7 has its own mean longitudinal direction 71 perpendicular to the axis 69. It is thus possible to orient it relative to the axis 5 by pivoting the blade carrier 70 about the axis 69 relative to the yoke 68 and to the body 6. In practice, the mean direction 71 specific to each blade carrier 70 intersects the reference surface 13 within an annular zone 76 thereof that is circularly symmetrical about the axis 5 having a minimum radius $R_3$ smaller than above-mentioned radius $R_2$ but nevertheless greater than the transparent zone of a cornea 2.

Means are provided for locking each blade carrier 70 adjustably with respect to rotation about its axis 69.

To this end, each yoke 68 has a zone 72 that projects approximately parallel to the axis 5 relative to the face 52 of the shoulder 50 towards the base portion 7 of the support 4, said zone 72 being set back towards the inside of the support 4 relative to the reference surface 13 and not making contact with any portion of the support 4, even though said zone 72 is situated further from the axis 5 than is the blade carrier 70.

By means of said zone 72, the yoke 68 carries a ring 73 that is rotatable about an axis 74 but that cannot move in translation along said axis 74. The axis 74 is situated in the plane 205, being offset relative to the axis 69 towards the base portion 7 of the support 4, and being perpendicular to the direction 71 of the blade carrier 70, relative to which said axis 7 is fixed.

The ring 73 is thus disposed on the opposite side of the zone 72 to the side thereof that faces the axis 5, in a position disengaged by the base portion 7 of the support 4 when said portion is separated from the head portion 8, thereby enabling mutual rotation to be performed. As shown in FIG. 8, the ring 73 carries graduation marks 80 that are visible when the base portion 7 is separated in this way from the head 8, said graduations being given in mm, for example, and corresponding to incision diameters. In addition, the zone 72 of the yoke 68 or the blade carrier 70 itself carries a reference mark 75, e.g. in the form of a single line.

Figure 11:
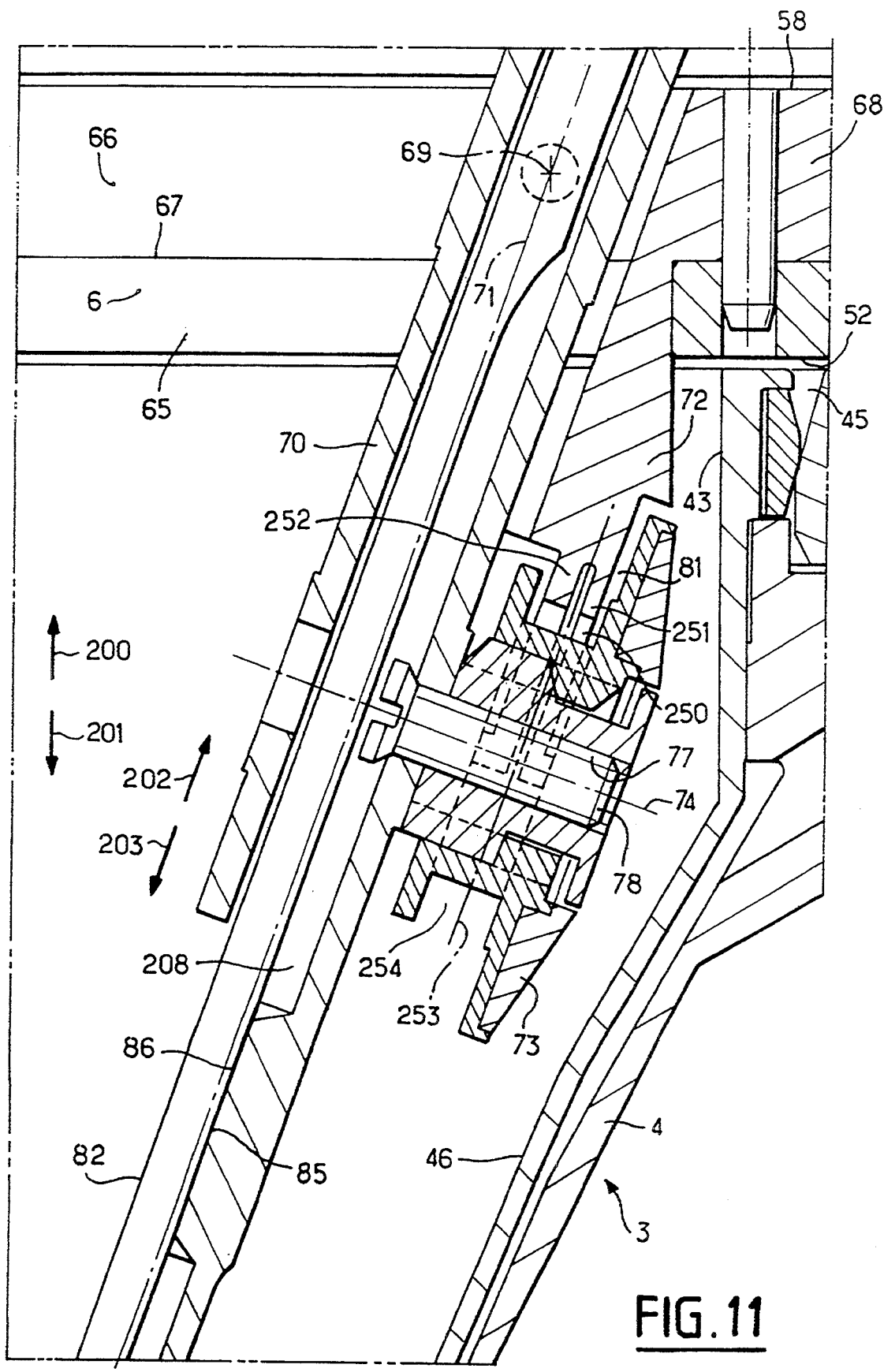
FIG. 11 shows a portion of FIG. 1 on a larger scale.

As shown in FIG. 11, the ring 73 has a micrometer tapping 77 about the axis 74 and engaging with a coaxial screw 78 securely mounted on the blade carrier 70. By rotating the ring 73, the distance between the blade carrier 70 and the zone 72 of the yoke 68 can be adjusted at the axis 74, i.e. the orientation of the longitudinal direction 71 of the blade carrier can be adjusted relative to the axis 5, and in particular the gap or offset $R_4$ between $R_2$ and $R_3$ and extending between the axis 5 and the point 79 of intersection between said direction 71 and the reference surface 13 can be adjusted within the limits of the zone 76 on the reference surface 13. This difference or offset $R_4$ determines an incision radius.

To make such motion possible, the ring 73 is mounted on the zone 72 of the yoke 68 by engaging a circularly symmetrical annular groove 254 about the axis 74, as shown in FIG. 11, which groove 254 in the ring 73 engages a slideway 81 on the zone 72 of the yoke 68. The slideway 81 is in the form of a fork that is open towards the base portion 7 and that includes two arms 250 disposed symmetrically about the plane 205 and that engage in the groove 254 on either side of the axis 74. Each of the arms 250 is itself split into two branches 251 and 252 towards the base portion 7, which branches are situated on opposite sides of a plane 253 extending approximately perpendicularly to the axis 74 and bearing in opposing manner parallel to said axis 74 in the groove 254. The branches 252 closest to the axis 5 are stiff, but the branches 251 furthest from the axis 5 have dimensions (as are easily determined by the person skilled in the art given the material from which the yoke 68 is made and suitably chosen for this purpose by said person skilled in the art) so as to be resilient in a manner that enables the two branches 251 and 252 to be permanently prestressed with respect to moving towards each other in the groove 254. While preventing the ring 73 from moving parallel to the axis 74 relative to the zone 72 of the yoke 68, and more particularly relative to the stiffer branches 252 of the arms 250, such a disposition makes it possible for the ring 73 to move relative to the axis 69 and it also enables the ring 73 to tilt about the zone 72 of the yoke 68.

Each blade carrier 70 is generally tubular in shape, being circularly symmetrical about its own elongate direction 71 and it delimits an internal channel 208 that slidably receives a blade 82 for sliding along its own longitudinal direction 71, said blade extending in rectilinear manner from a sharp end or tip 83 in the form of a lancet, as shown in FIG. 9 and directed towards the base portion 7, to a drive end 84 that projects out from the body 6 and the support 4 in the head portion 8 thereof. Respective flats 85 and 86 on the blade 82 and on the blade carrier 70 prevent relative rotation about the longitudinal axis 71 which also constitutes a mean longitudinal axis for the blade 82 passing through its tip 83.

The end 84 of each blade 82 co-operates with the corresponding blade carrier 70 via means 87 enabling the blade 82 to be displaced in controlled manner in translation along its own longitudinal direction 71 relative to the blade carrier 70 between two limiting positions:

a rest position in which the blade is shown in FIG. 1, where the blade is retracted into the body 6 and the support 4 in the direction of arrow 202 along its longitudinal direction 71 so as to be set back from the reference surface 13 with which the tip 83 then lies flush; and a cutting position shown diagrammatically in FIG. 1 by means of dot-dashed lines, where the tip 83 projects out from the body 6 and the support 4 in the direction of arrow 203 opposite to arrow 202 and relative to the reference surface 13 which the blade 82 then cuts while keeping to the adjusted offset R₄ relative to the axis 5, the magnitude of said projection being adjustable by acting on means 87 which are independent for each of the blades 82.

To this end, the end 84 of each blade 82 carries an adjustment knob 88 that projects beyond the blade carrier 70 at its end opposite from its tip 83. The knob 88 is rotatably mounted about the longitudinal axis 71 of the blade 82 and is secured in translation relative to the blade carrier 70 in said longitudinal direction 71. The knob 88 carries graduations 89 that are expressed, for example, in tenths of a millimeter, said graduations corresponding to the extent whereby the tip 83 of the blade 82 projects relative to the reference surface 13 when in its cutting position.

The knob 88 carries a thread 90 whereby it engages in tapping 91 in a sleeve 92 mounted to move in translation along the longitudinal axis 71 both relative to the adjustment knob 88 and relative to the blade carrier 70. The sleeve 92 thus locally surrounds the knob 88 over its thread 90 and also locally surrounds a length 93 of the blade 82 situated between the head portion 8 of the support 4 and the end 84.

The sleeve 92 can move in translation along the longitudinal axis 71 relative to the blade carrier 70 and also relative to the knob 88 and to the blade 82, however it is prevented from rotating relative to the blade carrier 70 by keying 94 in an end zone 95 of the blade carrier 70 surrounding the sleeve 92, and projecting from the head portion 8 of the support 4 in the direction 202 between the end 84 of the blade 82 and the axis 69.

To co-operate with the graduations 89 of the adjustment knob 88, the sleeve 92 carries a reference 97 on a ring 96 that surrounds the drive knob 88, which reference 97 may be in the form of a radial line relative to the longitudinal direction 71, as shown in FIG. 10, thereby making it possible to identify the relative angular position between the adjustment knob 88 and the sleeve 92, i.e. also the blade carrier 70, about the longitudinal direction 71, i.e. making it possible to display the amount the tip 83 of the blade 82 projects relative to the reference surface 13 when the blade 82 is in its cutting position. The end zone 95 of the blade carrier 70 surrounds the outside of the sleeve 92, and a compression spring 98 interposed thereby at this level and prestressed in the longitudinal direction 71 tends to urge the sleeve 92 resiliently in translation along the longitudinal direction 71 relative to the blade carrier 70 towards the axis 69 and towards the inside of the support 4, i.e. in the direction 203.

Between the end zone 95 of the blade carrier 70 and the adjustment knob 88, the outside of the sleeve 92 has an annular shoulder 99. This shoulder faces in the direction 203 towards the axis 69 and it bears in said direction against an opposing shoulder 100 inside a trip knob 101 surrounding the sleeve 92 away from the end zone 95 of the blade carrier 70, with the trip knob 101 being free to rotate about the longitudinal direction 71 relative to the sleeve 92 and being also free to move in translation along said longitudinal direction 71, said motion nevertheless being restricted to limit set firstly by mutual contact between the shoulders 99 and 100, and secondly by maximum compression of the spring 98.

Facing each other, the trip knob 101 and the blade carrier 70 themselves have mutual abutment means in the zone 95 in the longitudinal direction 71, thereby enabling two stable relative positions to be taken up in said longitudinal direction 71 depending on the relative angular position thereof about said longitudinal direction.

More precisely, towards the end zone 95 of the blade carrier 70 in the direction 203, the trip knob 101 has alternating radial ribs 102 and grooves 103, the ribs 102 having end flats 104 in the direction 203 that extend perpendicularly to the longitudinal direction 71. The end zone 95 of the blade carrier 70 has alternating radial ribs 105 and grooves 106 towards the trip knob 101 in the direction 202, which ribs and grooves are complementary to the grooves 103 and ribs 102, the ribs 105 having plane end flats 107 in the direction 202 that extend perpendicularly to the longitudinal direction 71.

The blade 82, the blade carrier 70, the adjustment knob 88, the sleeve 90, and the trip knob 101 are dimensioned in a manner that is easily determined by the person skilled in the art such that:

when the respective flats 104 and 107 of the ribs 102 and 105 are placed so as to bear mutually against each other in the longitudinal direction 71 and with the adjustment knob 88 oriented so that the digit zero is displayed on the graduations 89 in association with the reference mark 97 of the sleeve 92, the blade 82 is placed in a position such that its tip 83 is set back from the reference surface 13 by an amount such that should the ribs 102 subsequently be brought into coincidence with the groove 106 and the ribs 105 be brought into coincidence with the grooves 103 by rotating the trip knob 101, then the effect of the spring 98 is to cause the trip knob assembly 101, the sleeve 92, the adjustment knob 88, and the blade 82 to move in translation in the direction 203 relative to the blade carrier 70 through an amplitude such that the tip 83 comes flush with the reference surface 13, as shown in FIG. 1; and by placing the trip knob 101 so that it presses again against the end zone 95 of the blade carrier 70 via the flats 104 and 107, and if the adjustment knob 88 then displays the maximum intended extension for the tip 83 of the blade 82 relative to the reference surface 93 (by means of the graduations 89 and the reference marks 97), then the tip 83 remains set back relative to the reference surface 13 until rotation is applied to the trip knob 101 such that its ribs and grooves correspond respectively with the grooves and ribs of the end zone 95 of the blade carrier 70, where upon the spring 98 causes the trip knob 101, the sleeve 92, the adjustment knob 88, and the blade 82 to move suddenly in the direction 203 relative to the blade carrier 90 until the tip 83 of the blade 82 is caused to project from the reference surface 13 by an amount that corresponds to the value displayed by means of the adjustment knob 88.

Thus, prior to placing the keratotome 3 on the anterior face 1 of the cornea 2, the surgeon can adjust the offset R₄ of the intersection between the longitudinal direction 71 and the reference surface 13 relative to the axis 5 by means of the ring 73, and this can be done independently for each of the blades 82, while the head portion 7 is disassembled from the body portion 8, after which these two portions can be reassembled, thereby enabling the surgeon to use the adjustment knob 88 to set independent incision depths for the blades 82 while these blades 82 remain in a rest position, i.e. set back from the reference surface 13. After disposing the apparatus on the anterior face of the cornea 2 with the axis 5 thereof coinciding with the visual axis, and after locking it in place by establishing suction in the cavity 9 or by engaging the teeth 31 against the cornea, the surgeon can cause each of the blades 82 to move suddenly into its preadjusted projecting position relative to the reference surface 13 merely by rotating the trip knobs 101, in other words the surgeon can cause each blade 82 to penetrate to a preadjusted depth into the cornea 2.

Thereafter, by acting on the drive means 61, the surgeon causes the body 6 to rotate relative to the support 4, thereby giving rise to identical rotation of the two blades 82 about the visual axis and relative to the cornea 2, i.e. the surgeon can make arcuate incisions having the same angular length.

In order to enable the surgeon to monitor, and preferably to preadjust, both the angular position of the arcuate incisions and the angular magnitude thereof, the keratotome 3 of the invention includes means for determining the relative angular position of the support and the body about the axis 5, which means 108 are described below with reference to FIGS. 1, 2, and 3, as implemented in a preferred embodiment.

In this embodiment, said means 108 comprise, in particular, in the head portion 8 of the support 4 a coaxial ring 109 which is secured thereto but with the possibility of having its angular position adjusted.

To this end, the ring 109 (which is made of spring steel or the like) has a cylindrical outer peripheral face 110 of a diameter that is identical to the diameter of the face 44 when said ring is assembled to the support 4, with the face 110 of the ring 109 then coming into the immediate proximity of the face 58 of the shoulder 49 of the body 6 all the way to the face 47. The ring 109 also projects above the face 47. At a level that corresponds substantially to the level of the face 47, the face 110 is hollowed out in the form of a continuous annular groove 111 that engages on a continuous annular rim 112 on the support 4, which rim projects from the face 44 towards the axis 5 where said face 44 engages the face 47.

The ring 109 is axially defined by a plane annular face 113, and by a circular edge 114 that connects to the face 113, and by an inside peripheral face 116 which is essentially in the form of a tapering body of revolution about the axis 5, except locally, as explained below.

The ring 109 has a discontinuity in the form of a gap 117, thereby making it elastically compressible radially, and it is mounted relative to the support 4 so that its face 110 comes into abutment against the face 44 of the support 4, which thus constitutes a friction bearing surface therefor.

However, when voluntary manual force is applied to the ring 109 in a circumferential direction so as to tend to close the gap 117, then the diameter of the face 110 of the ring 109 is reduced, and consequently it can be rotated at will about the axis 5 relative to the support 4 before being secured thereto again by releasing said manual force.

In order to enable such force to be applied, the portion of the ring 109 that projects relative to the face 47 of the support 4 on either side of the gap 17 has manual grasping means in the form of two notches 108 that leave a lug 119 between themselves and the gap 117, thus providing the surgeon's fingers with purchase towards the gap 117.

In an inner peripheral zone 120 that does not include the gap 117 and that extends over an arc $\alpha_3$ of 180°, the frustoconical inner peripheral face 116 is not directly connected to the face 113 of the ring 109, with such connection occurring via an inner peripheral face 121 that is circularly cylindrical about the axis 5 and towards which said face 121 faces. At beth ends, relative to a circumferential direction centered on the axis 5, the face 121 connects via an abutment shoulder 122 to the frustoconical inner peripheral face 116.

In addition, the body 6 carries two abutment tabs 124 projecting parallel to the axis 5 on the face 58 of the shoulder 49 and in the manner that is adjustable within a zone of said face 58 that remains disengaged by the ring 109. The abutment tabs 124 are placed to face the inner peripheral zone 120 of the ring 109 and are suitable for coming circumferentially into abutment against one or other of shoulders 122 in either direction of rotation 206 or 207 of the body 6 relative to the support 4. These abutment tabs 124 are symmetrical about the plane 204 from which they are each offset by less than 90°, respectively in the direction 206 and in the direction 207.

To this end, the face 58 of the body 6 has a plurality of identical blind holes 125 that are circularly cylindrical about respective axes 126 uniformly distributed about the axis 5 and equidistant therefrom, and each of the blind holes 125 is suitable for receiving one of the abutment tabs 124; in the preferred example as shown, there are thirteen blind holes 125 which are symmetrically distributed about the plane 204 at an angular pitch of $\alpha_4$ equal to 10° over a total angular extent of 120°; for example, each hole 125 is tapped, and each tab 124 is provided with a threaded rod 127 suitable for being screwed into a hole 125.

By securing the two tabs 124 to the body 6 in angular positions that are suitably chosen relative to the axis 5 and that are symmetrical about the plane 204, and insofar as each tab 124 is suitable for coming circumferentially into abutment against one of the shoulders 122 in the direction 206 or 207 of rotation of the body 6 relative to the support 4, rotation limits for the body 6 about the axis 5 relative to the support 4 can be fixed firstly with predetermined amplitude of relative rotation between the directions limited by adjusting the angular position of the tabs 124 on the body 6, and secondly with the angular positioning of said limiting orientations being adjusted relative to the support 4 by adjusting the angular position of the abutment shoulders 122 of the ring 109 relative thereto.

In this respect, the blind holes 125 act as graduations relative to the body 6 enabling the angular position of the body to be observed relative to the ring 109, i.e. relative to the support 4, in co-operation with the abutment shoulders 122 of the ring 109. Each of these blinds holes 125 is preferably also associated with a graduation 123 which, in the present example, is expressed as the value of the angular offset between the axis 126 of the blind hole 125 in question about the axis 5 and relative to the plane 205, said value being expressed in degrees. Thus, a blind hole 125 whose axis 126 lies in the plane 204 carries the number 90 as a graduation 123, and the blind holes 125 that follow one another in succession from said blind hole 125 on either side of the plane 204 carry the numbers 80, 70, 60, 50, 40, and 30, respectively.

Before causing the blades 82 to move suddenly from their rest positions to their cutting positions, but after securing the keratotome 3 in an appropriate position on the anterior face 1 of the cornea 2, it suffices for the surgeon to use the means 61 to bring the body 6 into an orientation such that one of the tabs 124 is in abutment against the corresponding shoulder 122, and then after causing the blades to be extended suddenly, the surgeon causes the body 6 to rotate relative to the support 6 until the other tab 124 comes into abutment against the other shoulder 122, thereby ensuring that incisions are made of predetermined angular amplitude, and also in positions that are likewise predetermined.

In order to facilitate the prior adjustments, the body 6 preferably also includes means 128 for identifying an axis of astigmatism, e.g. in a manner suitable for removably securing to the body 6, at the same time as that one of the abutment tabs 124 which is offset in the direction 206 relative to the plane 204 in the example shown. This may be done by clamping said tab and the face 58 of the shoulder 49 of the body 1 together such that said adjustment means lie in a common plane that includes the axis 5 and the common axis 126 of said tab 124 and of the hole 125 that receives it; which plane coincides with the plane referenced IX—IX in FIG. 2.

Figure 2:
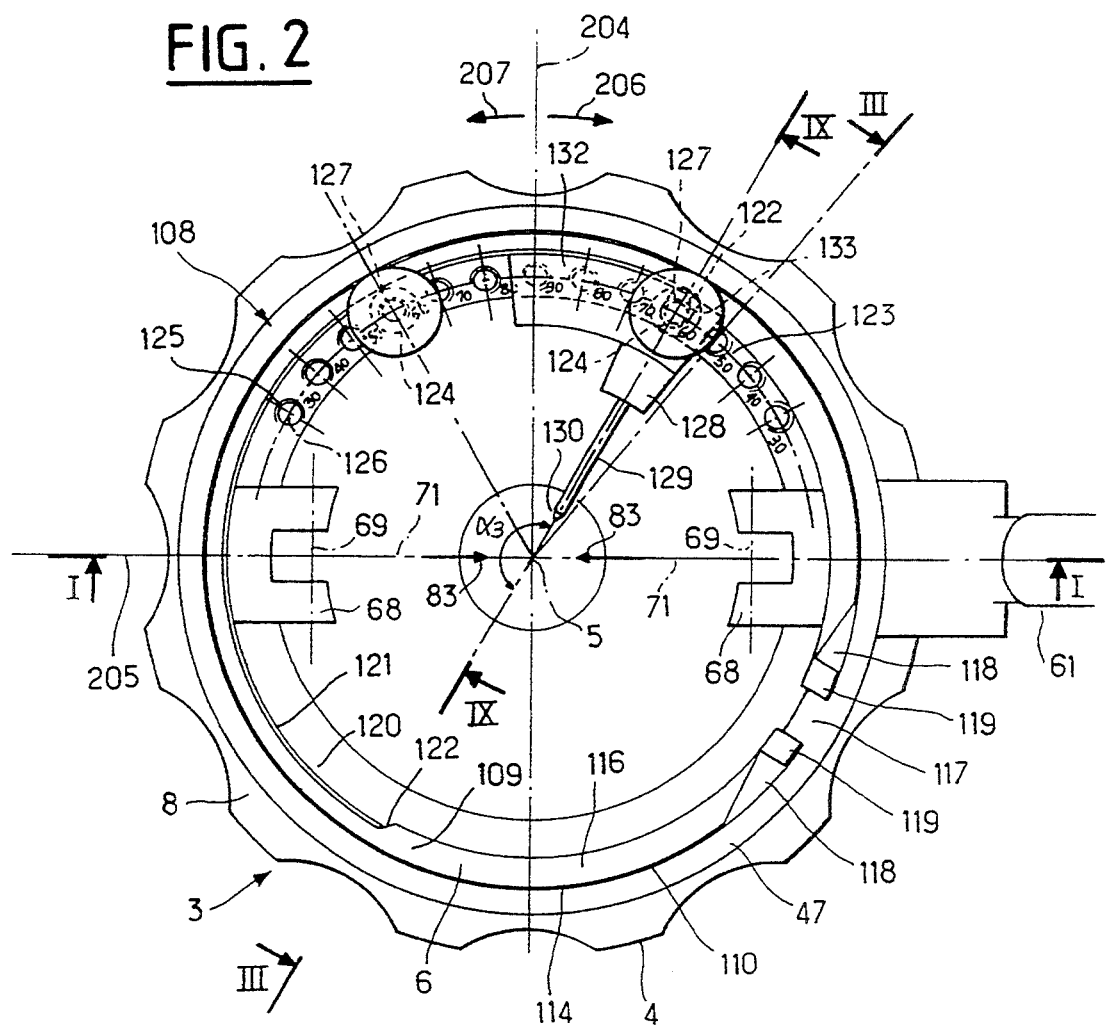
FIG. 2 is a fragmentary plan view of the keratotome, i.e. it shows the keratotome as it appears at its end opposite from its base portion, parallel to the axis of relative rotation between the inner body and the outer support and in the direction marked by arrow II in FIG. 1; for reasons of clarity, the blades and the blade carriers are omitted from this figure, as is the detail of the means for driving the body to rotate relative to the support.
Figure 3:
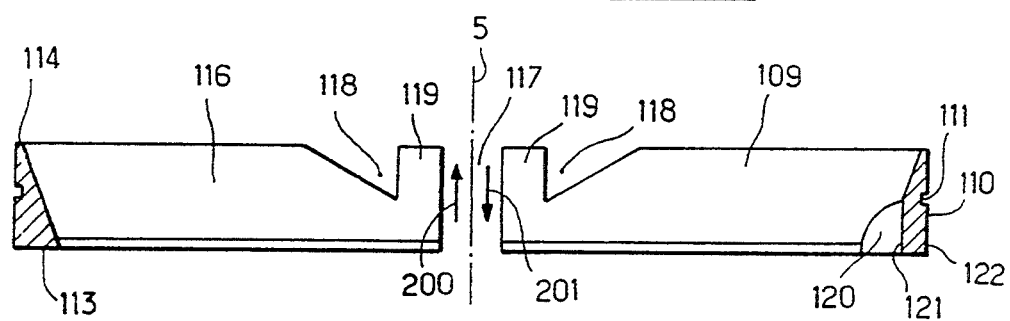
FIG. 3 is a view of a ring carried by the support, and shown in section on two half-planes that include the axis of relative rotation between the inner body and the outer support, and marked III—III in FIG. 2, the angular position of the ring being adjustable about the axis of relative rotation between the body and the support and the ring itself carrying the abutments provided on the support for limiting rotation of the body.

In particular, FIGS. 2, 6, and 7 show means 128 for marking an astigmatism axis and designed in the above manner. These means are provided in the form of a needle 129 which (as shown in FIG. 7) converges towards the axis 5 in a direction running from the head portion 8 towards the foot portion 7, while remaining fully set back relative to the reference surface 13.

Towards the axis 5 and towards said reference surface 13, the needle 129 has a bend terminated by a free pointed end 130 which terminates at the axis 5 in the vicinity of the surface 13 of the reference, such that said point constitutes the reference mark to be superposed on the mark identifying the visual axis of the patient, whereas at the opposite end it is securely imprisoned by another end 131 in an intermediate assembly part 132 suitably shaped to locally engage the faces 65, 67, 66 of the body 6 and also the face 58 of the shoulder 49 thereof, with this taking place in a forked zone 133 suitable for inserting between the respective tab 124 and the face 58, around the rod 127 of said tab 124.

Under such conditions, the angular length of each incision and the angular position thereof can be adjusted as follows, it being assumed that the depth and the diameter of the incision are already adjusted and each of the blades being assumed to be in its rest position:

the angular extent of each of the incisions to be made is determined with reference to the visual axis;

respective tabs 124 are screwed into those two holes 125 whose graduations 123 correspond to one-half of the angular extent selected for the incision, by fixing the means 128 by means of the tab 124 offset in the direction 206 about the plane 104;

the ring 109 is rotated relative to the support 4 so as to bring the tab 124 provided with the means 128 into contact with the associated abutment shoulder 122 without rotating the body 6 relative to the support 4;

after the keratotome has been appropriately placed and secured on the cornea, in particular by bringing the tip 130 into coincidence with the mark specifying the visual axis of the patient, and by orienting the manual control means 61 in a manner that is convenient for the surgeon, the ring 109 and the body 6 may optionally be rotated simultaneously relative to the support 4 while maintaining the above-mentioned contact between the tab 124 provided with the means 128 and the associated abutment shoulder 122, thereby bringing the needle 129 into coincidence with the astigmatism axis as previously marked on the anterior face 1 of the cornea 2;

the blades are caused to move into their cutting positions, and without rotating the ring 109 relative to the support 4, the body 6 is caused to rotate relative thereto in the direction 207 until the other one of the tabs 124 comes into contact with the other one of the shoulders 122, thereby causing the desired incisions to be made; and the blades are retracted to their rest position and the keratotome is separated from the cornea.

In the example shown in FIG. 2, in particular, two arcuate incisions are thus made simultaneously each over an angular extent of 120°, and each uniformly distributed on either side of the axis of the astigmatism, by placing the two tabs 124 in the blind holes 125 that are marked by the numbers 60 constituting graduations 123, and in the embodiment described, the keratotome of the invention thus makes it possible to perform a range of incisions having respective angular extents lying in steps of 20° between 60° (in which case the tabs 124 must be placed in the blind holes 125 marked with the number 30), and 180° (in which case a single tab 124 must be placed in the blind hole 125 marked by the number 90), but without going beyond the ambit of the present invention other ways of varying the angular extent of the incisions that can be made using a keratotome of the invention are available, as are other limit values on said angular extent.

What is claimed is:

1. A keratotome for making an incision in a cornea, and comprising, for this purpose:

an envelope-forming tubular outer support having a determined axis and including, for application against a cornea, an annular base portion that is circularly symmetrical about the axis of the support and that defines a reference geometrical surface determined by the shape presented by the cornea when the support has its base portion pressed thereagainst;

a tubular inner body disposed coaxially inside the support and set back towards the inside of the support relative to the reference surface;

guide means for guiding the body in rotation about the axis relative to the support;

drive means for driving the body in rotation about the axis relative to the support;

at least a blade disposed inside the body and extending along a longitudinal direction, the blade having a sharp tip in a determined direction relative to its longitudinal direction; and means for providing a connection between the blade and the body, said means including means for displacing the blade in controlled manner in translation along its longitudinal axis relative to the body between a rest position, in which it is set back towards the inside of the support relative to the reference surface, and in which the tip is directed towards said reference surface, and in a cutting position where the tip projects outside from the support relative to the reference surface, in a manner that is offset relative to the axis of the support;

wherein, in order to perform arcuate incisions of determined angular position and of determined angular length, the support and the body have determining means for determining their relative angular position which include abutments defining two limiting relative angular positions between the support and the body and carried respectively by the support and by the body.

2. A keratotome according to claim 1, wherein the determining means include graduation forming means forming graduations for marking angular position relative to the support and the body and carried respectively by the support and by the body.

3. A keratotome according to claim 1, wherein the support carries a coaxial ring that is angularly adjustable in position and that carries said abutments that are integral therewith and that are offset by 180° from each other, and wherein said abutments carried by said body are angularly adjustable independently.

4. A keratotome according to claim 3, wherein the body carries means for marking the axis of astigmatism which are integral with one of said abutments.

5. A keratotome according to claim 3, wherein said ring is opened by a radial gap, which is elastically compressible radially and in centrifugal radial abutment against a coaxial annular bearing surface of the support under prestress such that it is temporarily secured to the support by friction, but with the gap nevertheless remaining open, and wherein it has grasping means on respective sides of said radial gap for the purpose of enabling manual force to be applied circumferentially in such a direction as to close the gap.

6. A keratotome according to claim 1, wherein:
another blade angularly is offset by 180° relative to the first blade and disposed inside the body along its own axial direction and having its own sharp tip in a determined direction along its longitudinal direction; and wherein
link means between said other blade and the body themselves include means for displacing the other blade in adjustable manner in translation along its own longitudinal direction relative to the body between a rest position in which said other blade is set back towards the inside of the support relative to the reference surface, and in which its tip points towards said reference surface, and a cutting position in which said tip projects out from the support relative to the reference surface so as to be offset relative to the axis of the support.

7. A keratotome according to claim 6, wherein the means for displacing each of the blades in adjustable manner in translation along its own longitudinal direction comprise:
means for displaying the adjusted value of said projection while the blade remains in its rest position; and
means for causing the blade to move voluntarily and suddenly from its rest position to its cutting position.

8. A keratotome according to claim 7, wherein said means for displacing each blade in adjustable manner in translation along its own longitudinal direction comprise:
a blade carrier attached to said body;
an adjustment knob placed to project beyond said blade carrier away from the tip and mounted to rotate about said longitudinal direction relative to the blade carrier, and constrained to move in translation with the blade along said longitudinal direction;
a sleeve mounted to move in translation relative to the adjustment knob and relative to the blade carrier, along said longitudinal direction, and constrained to rotate with the blade carrier about said longitudinal direction, and having a transverse shoulder extending transversely relative to said longitudinal direction and facing in a direction going from the rest position towards the cutting position;
threaded connection means between the adjustment knob and the sleeve;
micrometer graduations for identifying the relative angular position of the adjustment knob and of the sleeve about said longitudinal direction, and constituting means for displaying the adjusted value of said projection;
means for resiliently urging the sleeve in translation relative to the blade carrier along said longitudinal direction in a direction going from the rest position towards the cutting position;
a trip knob mounted to rotate relative to the adjustment knob, to the sleeve, and to the blade carrier, and having a shoulder extending transversely relative to said longitudinal direction and facing in a direction going from the cutting position towards the rest position, and bearing against said transverse shoulder of the sleeve; and
mutual abutment means between the trip knob and the blade carrier in said longitudinal direction, comprising on the trip knob alternating radial ribs and grooves about said longitudinal direction and facing in a direction going from the rest position towards the cutting position, and on the blade carrier alternating radial grooves and ribs about said longitudinal direction, and facing in a direction going from the cutting position towards the rest position, and respectively complementary to the ribs and the grooves of the trip knob, said ribs and grooves being shaped so that mutual thrust between the trip knob and the blade carrier by means of said ribs as by engagement of said ribs in said grooves is stable.

9. A keratotome according to claim 8, including means for adjusting the offset value of the tip of each blade relative to the axis of the support in the cutting position, which means comprise:
hinge means for hinging the blade carrier to the body about a determined hinge axis offset relative to the axis of the support and set back towards the inside of the support relative to the reference surface, and perpendicular to the longitudinal direction of the blade and to a plane including the axis of the support; and
means for locking the blade carrier relative to the body in adjustable manner in rotation about the hinge axis.

* * * * *